(12) United States Patent
Fisher

(10) Patent No.: US 10,674,969 B2
(45) Date of Patent: Jun. 9, 2020

(54) DEVICE TO FACILITATE READING OF A CHEST TUBE DISPLAY

(71) Applicant: Kirkland Fisher, Belltort, NY (US)

(72) Inventor: Kirkland Fisher, Belltort, NY (US)

( * ) Notice: Subject to any disclaimer, the term of this patent is extended or adjusted under 35 U.S.C. 154(b) by 0 days.

(21) Appl. No.: 15/984,756

(22) Filed: May 21, 2018

(65) Prior Publication Data

US 2019/0350536 A1    Nov. 21, 2019

(51) Int. Cl.
*G03B 17/56*   (2006.01)
*A61B 5/00*    (2006.01)
*A61M 25/02*   (2006.01)
*A61M 27/00*   (2006.01)

(52) U.S. Cl.
CPC .......... *A61B 5/7445* (2013.01); *A61M 25/02* (2013.01); *A61M 27/00* (2013.01)

(58) Field of Classification Search
CPC .... G03B 17/561; G03B 17/563; A61B 5/7445
See application file for complete search history.

(56) References Cited

U.S. PATENT DOCUMENTS

| | | | | |
|---|---|---|---|---|
| 4,684,230 A | * | 8/1987 | Smith | F16M 11/24 248/176.1 |
| 8,882,088 B2 | * | 11/2014 | Chapman | F16F 15/022 267/140.11 |
| 2010/0150543 A1 | * | 6/2010 | Fong | F16M 13/00 396/428 |

* cited by examiner

*Primary Examiner* — Minh Q Phan
(74) *Attorney, Agent, or Firm* — The Iwashko Law Firm, PLLC; Lev Ivan Gabriel Iwashko

(57) ABSTRACT

A device to facilitate reading of a chest tube display, the device including a pole, a handle disposed at a first end of the pole, a connecting portion disposed at a second end of the pole, a base to connect to the pole via the connecting portion on a top surface of the base, and a camera holding portion disposed on the top surface of the base to hold a camera therein.

6 Claims, 2 Drawing Sheets

DEVICE TO FACILITATE READING OF A CHEST TUBE DISPLAY

BACKGROUND

1. Field

The present general inventive concept relates generally to a device to facilitate reading of a chest tube display.

2. Description of the Related Art

A chest tube is a medical device used to facilitate the drainage of the chest cavity of a patient, as well as collection and accurate measurement of the fluid drained. The chest tube itself is inserted into the chest cavity, and the fluid drains down through this tube into collection tubes. Of necessity, the collection tubes and the means by which the collected drainage data is displayed are located on the floor on a display, beside the patient's bed, thusly requiring one to bend down, kneel or in some way maneuver their body to achieve eye level reading of the display, which is located a few inches from the floor.

Therefore, there is a need for a more efficient and effective method of reading a display of a chest tube device.

SUMMARY

The present general inventive concept provides a device to facilitate reading of a chest tube display.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a device to facilitate reading of a chest tube display, the device including a pole, a handle disposed at a first end of the pole, a connecting portion disposed at a second end of the pole, a base to connect to the pole via the connecting portion on a top surface of the base, and a camera holding portion disposed on the top surface of the base to hold a camera therein.

The device may further include a plurality of wheels disposed on a bottom surface of the base to allow the device to roll on a ground.

The camera holding portion may include a tightening member to tighten the camera holding portion around the camera when the camera is inserted within the camera holding portion.

The tightening member may turn in a clockwise direction to tighten the camera holding portion, and the tightening member may turn in a counterclockwise direction to loosen the camera holding portion.

The device may further include a positioning member disposed at a front portion of the base to allow a kick-out stand of the chest tube display to slide thereinto.

The device may further include a positioning member disposed at a front portion of the base to attach to a front portion of the chest tube display.

The positioning member may facilitate consistent, focused picture capturing of at least a portion of the front portion of the chest tube display.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1:
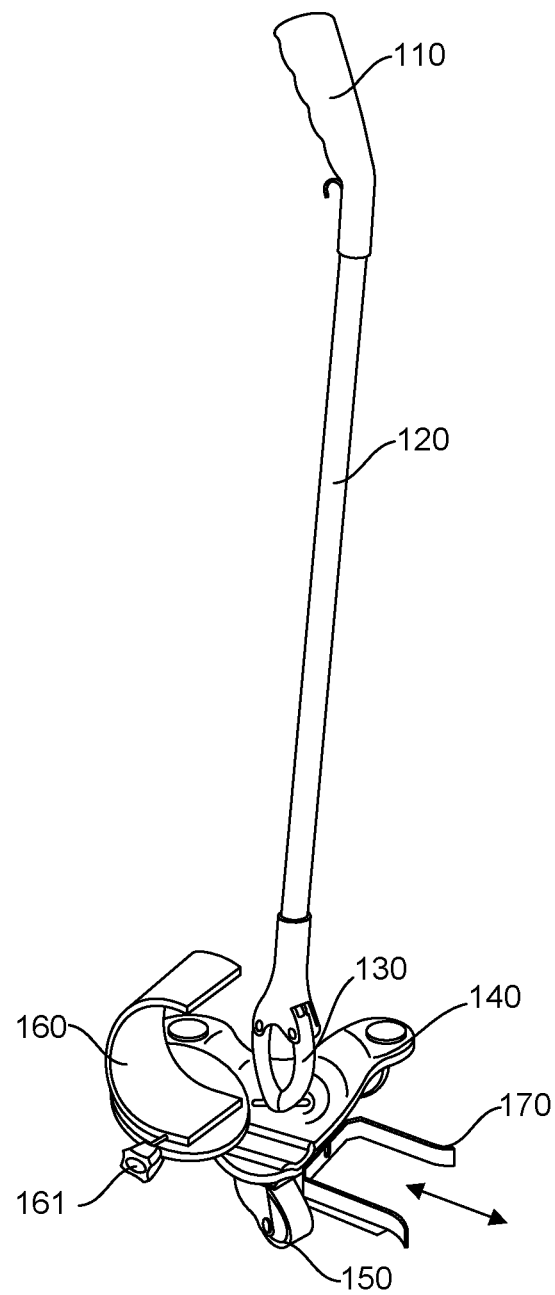
FIG. 1 illustrates a bottom perspective view of a device to facilitate reading of a chest tube display, according to an exemplary embodiment of the present general inventive concept.

FIG. 1 illustrates a bottom perspective view of a device 100 to facilitate reading of a chest tube display 10, according to an exemplary embodiment of the present general inventive concept.

Figure 2:
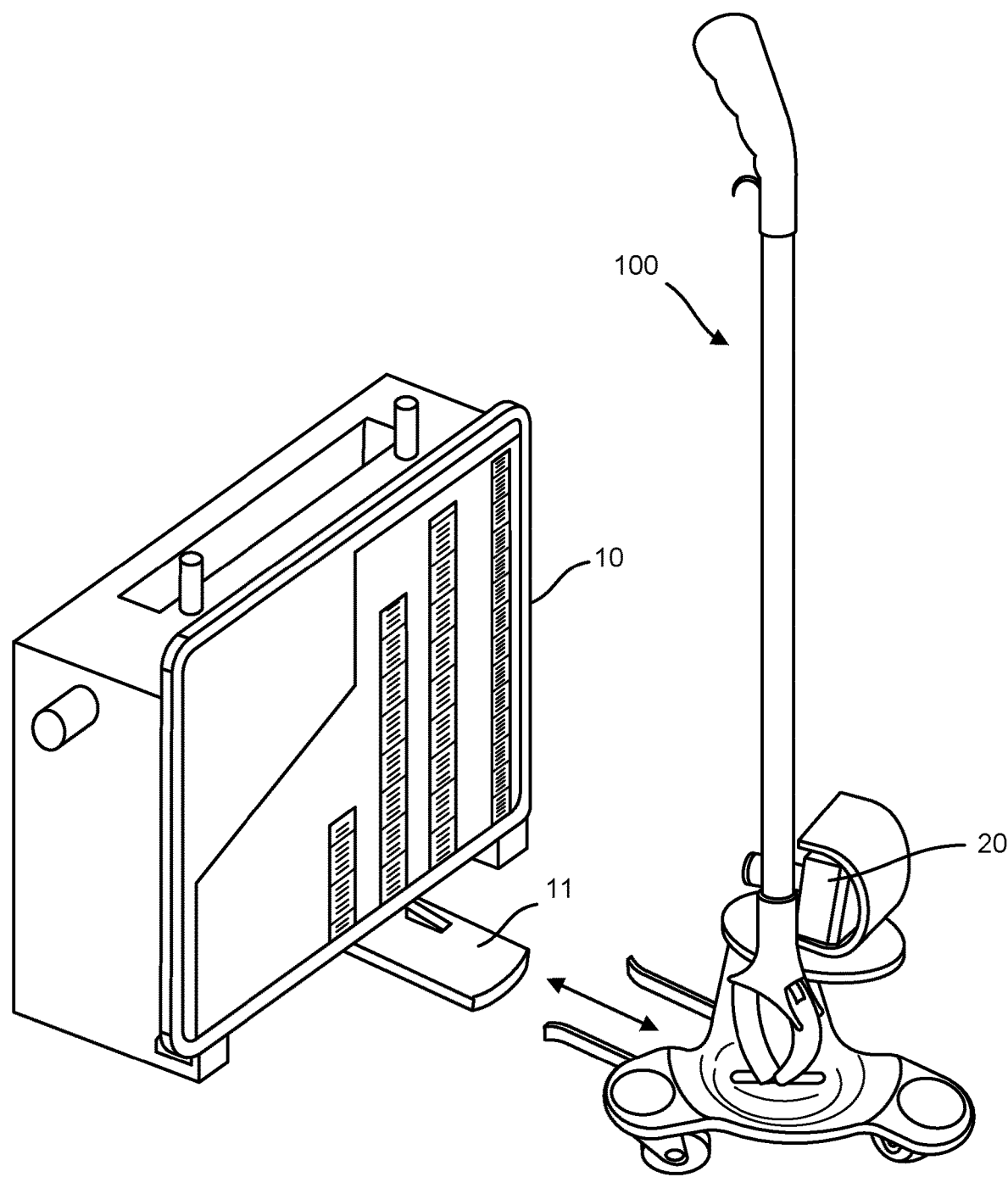
FIG. 2 illustrates the device with respect to the chest tube display, according to an exemplary embodiment of the present general inventive concept.

FIG. 2 illustrates the device 100 with respect to the chest tube display 10, according to an exemplary embodiment of the present general inventive concept.

The device 100, and components thereof, may be constructed from plastic, rubber, metal, silicone, wood, and any other material known to one of ordinary skill in the art.

Referring to FIG. 1, the device 100 may include a handle 110, a pole 120, a connecting portion 130, a base 140, a plurality of wheels 150, a camera holding portion 160, and a positioning member 170.

The handle 110 may be disposed at a first end of the pole 120, and may be utilized by a user as a grip of the device 100.

The connecting portion 130 may be disposed at a second end of the pole 120, and may be used to connect the pole 120 to a top surface of the base 140.

The base 140 may include the plurality of wheels 150 disposed at a bottom surface of the base 140.

The plurality of wheels 150 may swivel, and may be used to move the device 100 in a plurality of directions. In other words, the plurality of wheels 150 may allow the device to roll on a ground.

Referring to FIGS. 1 and 2, the camera holding portion 160 may be disposed on the top surface of the base 140, and may have a shape to hold a camera 20 therein, such as a semicircle, a clamp, a vice, etc., but is not limited thereto.

The camera 20 may be a digital camera, mobile device, or any other type of recording device that can record an image.

The camera holding portion 160 may include a tightening member 161, to tighten the camera holding portion 160 around the camera 20 when it is inserted within the camera holding portion 160. The tightening member 161 may be turned in clockwise and counterclockwise directions in order to tighten and/or loosen, respectively, the camera holding portion 160.

The positioning member 170 may be disposed at a front portion of the base 140, and may have a rectangular shape with a front portion of the rectangular shape removed. As such, the positioning member 170 may be disposed at the front portion of the base 140, in such a manner as to result in a device to-chest tube connection or association that readily facilitates consistent, focused picture capturing of at least a portion of the front portion of the chest tube display 10.

Also, end portions of sides of the positioning member may be curvedly flared outward. As such, the positioning member 170 may allow a kick-out stand 11 of the chest tube display 10 to be disposed therewithin, in order to stabilize the device 100 against the chest tube display 10 such that the camera 20 may take a good picture of the display.

As such, the user may view the camera 20 to see the results displayed on the display of the chest tube display 10.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A device to facilitate reading of a chest tube display, the device comprising:
   a pole;
   a handle disposed at a first end of the pole;
   a connecting portion disposed at a second end of the pole;
   a base to connect to the pole via the connecting portion on a top surface of the base;
   a camera holding portion disposed on the top surface of the base to hold a camera therein; and
   a positioning member disposed at a front portion of the base to allow a kick-out stand of the chest tube display to slide thereinto.

2. A device to facilitate reading of a chest tube display, the device comprising:
   a pole;
   a handle disposed at a first end of the pole;
   a connecting portion disposed at a second end of the pole;
   a base to connect to the pole via the connecting portion on a top surface of the base;
   a camera holding portion disposed on the top surface of the base to hold a camera therein; and
   a positioning member disposed at a front portion of the base to attach to a front portion of the chest tube display, such that the positioning member facilitates consistent, focused picture capturing of at least a portion of the front portion of the chest tube display.

3. The device of claim 2, further comprising:
   a plurality of wheels disposed on a bottom surface of the base to allow the device to roll on a ground.

4. The device of claim 2, wherein the camera holding portion comprises:
   a tightening member to tighten the camera holding portion around the camera when the camera is inserted within the camera holding portion.

5. The device of claim 4, wherein the tightening member turns in a clockwise direction to tighten the camera holding portion, and the tightening member turns in a counterclockwise direction to loosen the camera holding portion.

6. The device of claim 2, wherein the positioning member allows a kick-out stand of the chest tube display to slide thereinto.

* * * * *